United States Patent
Hares et al.

(10) Patent No.: US 10,456,206 B2
(45) Date of Patent: Oct. 29, 2019

(54) INSTRUMENT ARTICULATION

(71) Applicant: CAMBRIDGE MEDICAL ROBOTICS LTD, Cambridge (GB)

(72) Inventors: Luke David Ronald Hares, Cambridge (GB); Steven James Randle, Warwickshire (GB)

(73) Assignee: CMR SURGICAL LIMITED, Cambridge (GB)

( * ) Notice: Subject to any disclaimer, the term of this patent is extended or adjusted under 35 U.S.C. 154(b) by 449 days.

(21) Appl. No.: 15/111,460

(22) PCT Filed: Jan. 8, 2015

(86) PCT No.: PCT/GB2015/050019
§ 371 (c)(1),
(2) Date: Jul. 13, 2016

(87) PCT Pub. No.: WO2015/107326
PCT Pub. Date: Jul. 23, 2015

(65) Prior Publication Data
US 2016/0346939 A1 Dec. 1, 2016

(30) Foreign Application Priority Data

Jan. 14, 2014 (GB) .................................. 1400569.8
Oct. 15, 2014 (GB) .................................. 1418255.4

(51) Int. Cl.
B25J 17/00 (2006.01)
B25J 17/02 (2006.01)
(Continued)

(52) U.S. Cl.
CPC ........... *A61B 34/30* (2016.02); *B25J 17/0275* (2013.01); *B25J 17/0283* (2013.01); *A61B 2034/305* (2016.02)

(58) Field of Classification Search
CPC .......................... B25J 17/0275; B25J 17/0283
See application file for complete search history.

(56) References Cited

U.S. PATENT DOCUMENTS 4,511,305 A * 4/1985 Kawai ...................... B25J 9/046
414/735
4,557,623 A * 12/1985 Tella ....................... B25J 9/146
403/31

(Continued)

FOREIGN PATENT DOCUMENTS

EP 0200202 A2 11/1986
EP 0208495 A1 1/1987
(Continued)

OTHER PUBLICATIONS

International Search Report for GB148255.4 dated Jun. 9, 2015, 5 pages.

(Continued)

*Primary Examiner* — Jake Cook
(74) *Attorney, Agent, or Firm* — Dergosits & Noah LLP

(57) ABSTRACT

A robotic instrument comprising an arm extending between a robot arm connection and an attachment for an end effector, the arm comprising: a first arm part; a second arm part distal of the first arm part; and a joint whereby the first and second arm parts are coupled together, the joint permitting the first and second arm parts to rotate relative to each other about at least two mutually offset axes; a control rod attached to the second part of the arm at a location spaced from the first and second axes, the control rod extending distally of that location along the first arm part; and a drive mechanism for driving the control rod to move relative to the first arm part and thereby alter the attitude of the second arm part relative to the first arm part.

10 Claims, 8 Drawing Sheets

(51) Int. Cl.
*B25J 18/00* (2006.01)
*A61B 34/30* (2016.01)

(56) References Cited

U.S. PATENT DOCUMENTS

| | | | |
|---|---|---|---|
| 4,729,253 A | | 3/1988 | Rosheim |
| 4,805,477 A | | 2/1989 | Akeel |
| 5,692,412 A | * | 12/1997 | Rosheim .................... B25J 9/06 74/490.01 |
| 2008/0035701 A1 | | 2/2008 | Racenet et al. |

FOREIGN PATENT DOCUMENTS

| | | |
|---|---|---|
| EP | 1695669 A1 | 8/2006 |
| WO | 8704539 A1 | 7/1987 |
| WO | 8905216 A1 | 6/1989 |
| WO | 0030557 A1 | 6/2000 |
| WO | 2007146987 A2 | 12/2007 |
| WO | 03001986 A2 | 1/2013 |

OTHER PUBLICATIONS

Publication and International Search Report for PCT/GB2015/050019 dated Jun. 12, 2015, 29 pages.

\* cited by examiner

INSTRUMENT ARTICULATION

CROSS-REFERENCE

This is a United States national phase application of PCT/GB2015/050019 filed Jan. 8, 2015 entitled "Instrument Articulation," which claims priority from United Kingdom Application No. 1400569.8 filed Jan. 14, 2014 entitled "Instrument Articulation" and United Kingdom Application No. 1418255.4 filed Oct. 15, 2014 entitled "Instrument Articulation," the entire disclosures of which is incorporated herein by reference.

TECHNICAL FIELD

This invention relates to articulations, for example for surgical robots.

BACKGROUND

A typical robot arm comprises a series of rigid links, each of which is connected to the next by a respective articulation. Each articulation is designed to have appropriate characteristics of strength, range of motion, size etc. for the purpose the arm is to perform.

One particular application of robots is for performing or assisting in surgery. FIG. 1 illustrates a typical surgical robot arm. A patient 1 is lying on a bed 2. The robot arm 3 extends from a base 4 towards the patient. The arm has a series of rigid links 5, 6, 7, which are connected to each other and to the base by articulations 8, 9, 10. The articulations provide a sufficient range of motion that the arm can approach the patient in different ways so as to perform a range of surgical procedures. The links can be made to move about the articulations by motors 11 which are under the control of a surgeon. The final link 7 of the arm terminates in a wrist articulation 12 to which a surgical instrument 13 is attached. The surgical instrument is designed for insertion into the patient and, for example, could be an endoscope or could terminate in a cutting or pinching tool.

It is desirable for the tip of the surgical instrument to be articulated and hence mobile, so that it can be placed in a wide range of orientations relative to the remainder of the surgical instrument. That assists in allowing the surgical instrument to perform a wide range of surgical procedures, and in allowing a surgeon to place multiple arms close to a surgical site. It is also desirable for the surgical instrument articulation to be kinematically well-functioning, without there being any attitudes in the core of its range of motion that are difficult to reach or where there could be poor control over the motion of the end effector.

U.S. Pat. No. 4,257,243 describes a constant velocity joint for coupling a tractor drive shaft to an agricultural machine. U.S. Pat. No. 3,470,712 describes a similar arrangement for serving as a constant velocity coupling.

SUMMARY

According to the present invention there is provided a robot, robot arm or articulation as set out in the accompanying claims.

BRIEF DESCRIPTION OF THE DRAWINGS

The present invention will now be described by way of example with reference to the accompanying drawings. In the drawings.

DETAILED DESCRIPTION

Figure 1:
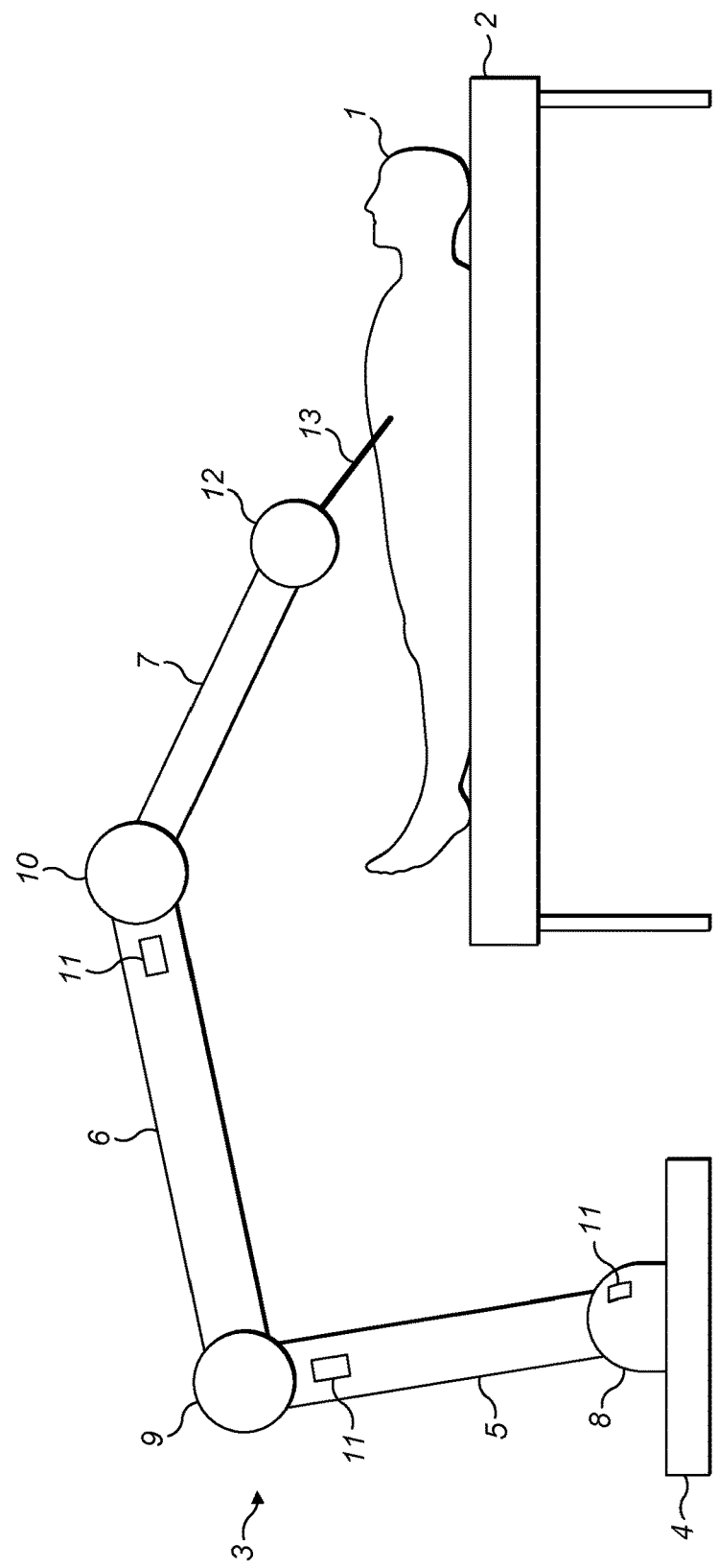
FIG. 1 shows a surgical robot arm.
Figure 2:
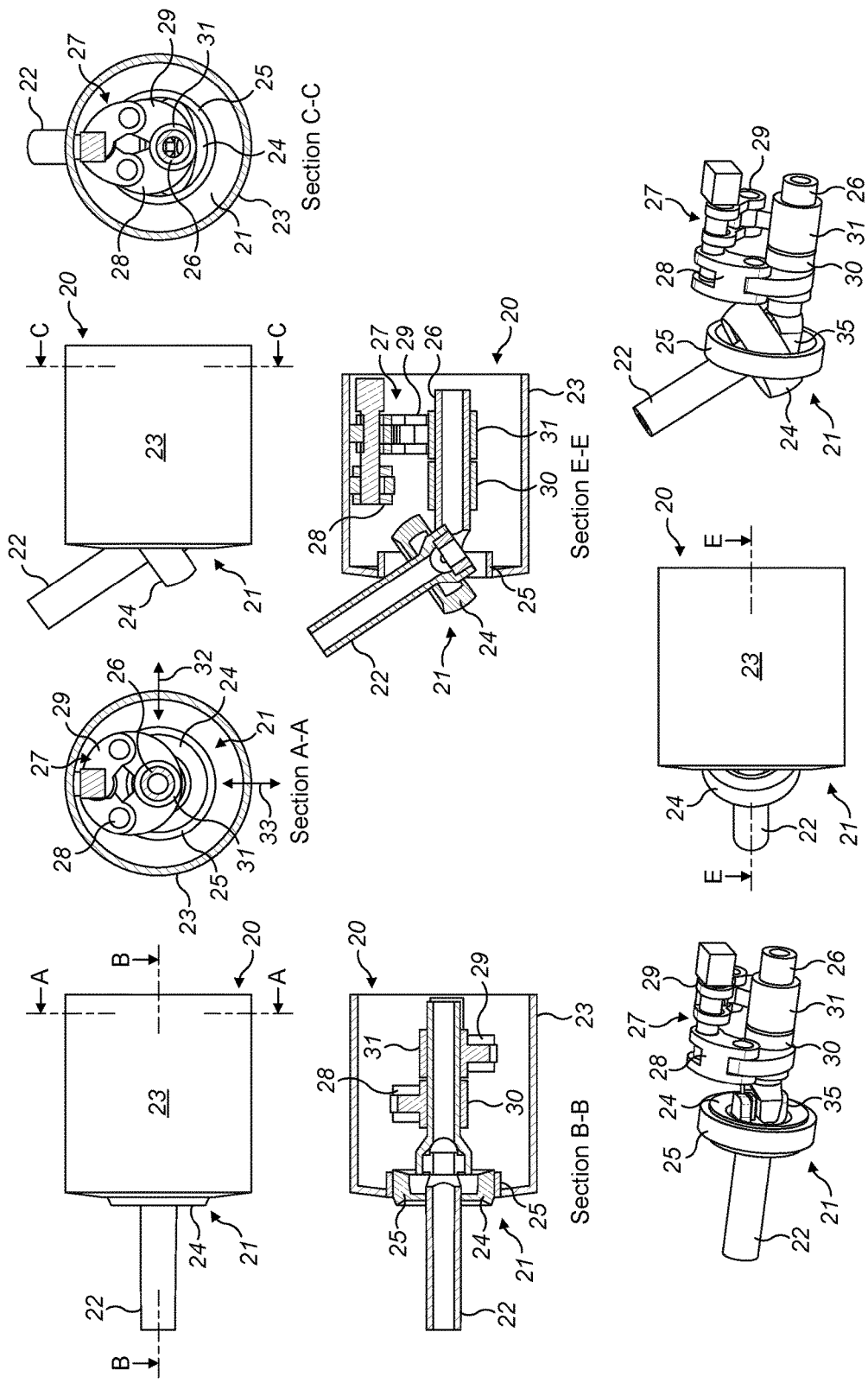
FIG. 2 shows various views of a first wrist joint for a surgical instrument.

FIG. 2 shows the terminal part of a surgical instrument. The surgical instrument is attached to a robot arm which is generally of the type shown in FIG. 1, with a base and a number of inter-articulated rigid links. The end-most part of the terminal link of the surgical instrument is shown at 20 in FIG. 2. The terminal link of the surgical instrument ends in a wrist joint 21 which carries an attachment 22 to which a surgical end effector can be attached, for example a cutting or pinching tool. The joint 21 articulates the attachment 22 relative to the terminal link 20 of the surgical instrument.

The terminal link of the surgical instrument is a rigid shaft, defined by a stiff outer tube 23. At the distal end of the tube is a spherical joint 21. Spherical joint 21 comprises a part-ball 24 which is captive in a part-cup 25. The part-cup is fast with the terminal link 20 of the surgical instrument. The part-ball is fast with the attachment 22. The spherical joint allows the attachment to move with three degrees of rotational freedom, but no translational freedom, relative to the terminal link of the surgical instrument.

On the interior of the part-ball 24 is a Hooke's or universal joint 35. The Hooke's joint is offset from the centre of rotation of the spherical joint 21 and connects the part-ball 24 to a control rod 26. The control rod runs through the interior of the tube 23 towards the proximal end of the terminal link 20 of the surgical instrument. The universal joint 35 connects the control rod to the tube so that it has two degrees of rotational freedom relative to the part-ball.

A pantograph mechanism 27 couples the control rod 26 to the tube 23. The pantograph comprises a pair of hinged two-part links 28, 29 which terminate in collars 30, 31 through which the control rod 26 runs. The pantograph permits the control rod to have three degrees of translational freedom relative to the tube 23, and to rotate relative to the tube about its longitudinal axis by spinning in the collars, but prevents the control rod from yawing about its transverse axes. The control rod is preferably rigid.

With this mechanism, when the control rod translates laterally relative to the tube, as indicated by axes 32 and 33 in FIG. 2, this causes the centre of the Hooke's joint 35 to move laterally. That in turn causes rotation of the spherical joint 21, which alters the direction of the attachment 22 relative to the terminal link 20 of the surgical instrument. In this way, when an end effector is coupled to the attachment the attitude of the end effector can be altered.

The motion of the control rod relative to the tube can be driven by any suitable means, for example electric motors or hydraulic or pneumatic rams. The control rod can be elongated so that it runs from the distal end of the terminal link 20 to near the proximal end of the terminal link, with the result that those drive means can be located near the proximal end of the terminal link. That is convenient because it reduces the weight that is suspended near the distal end of the terminal link, making the terminal link easier to control.

A further advantage of the mechanism described above is that the spherical joint 21 is relatively compact, meaning that when the attachment 22 is deflected at a significant angle to the terminal link 20 the terminal end of the surgical instrument can be brought relatively close to a patient on whom the robot is operating. The compactness of the joint also allows multiple similar robot arms to work in close proximity.

The pantograph mechanism for maintaining the direction of the control rod could be replaced with another mechanism for achieving the same purpose, for example a set of interlinked rockers running between the inner wall of the tube and the control rod and terminating in slip rings in which the control rod runs. Alternatively, the control rod could be permitted to yaw relative to the tube. For example the control rod could run through a spherical joint mid-way along the tube.

Figure 3:
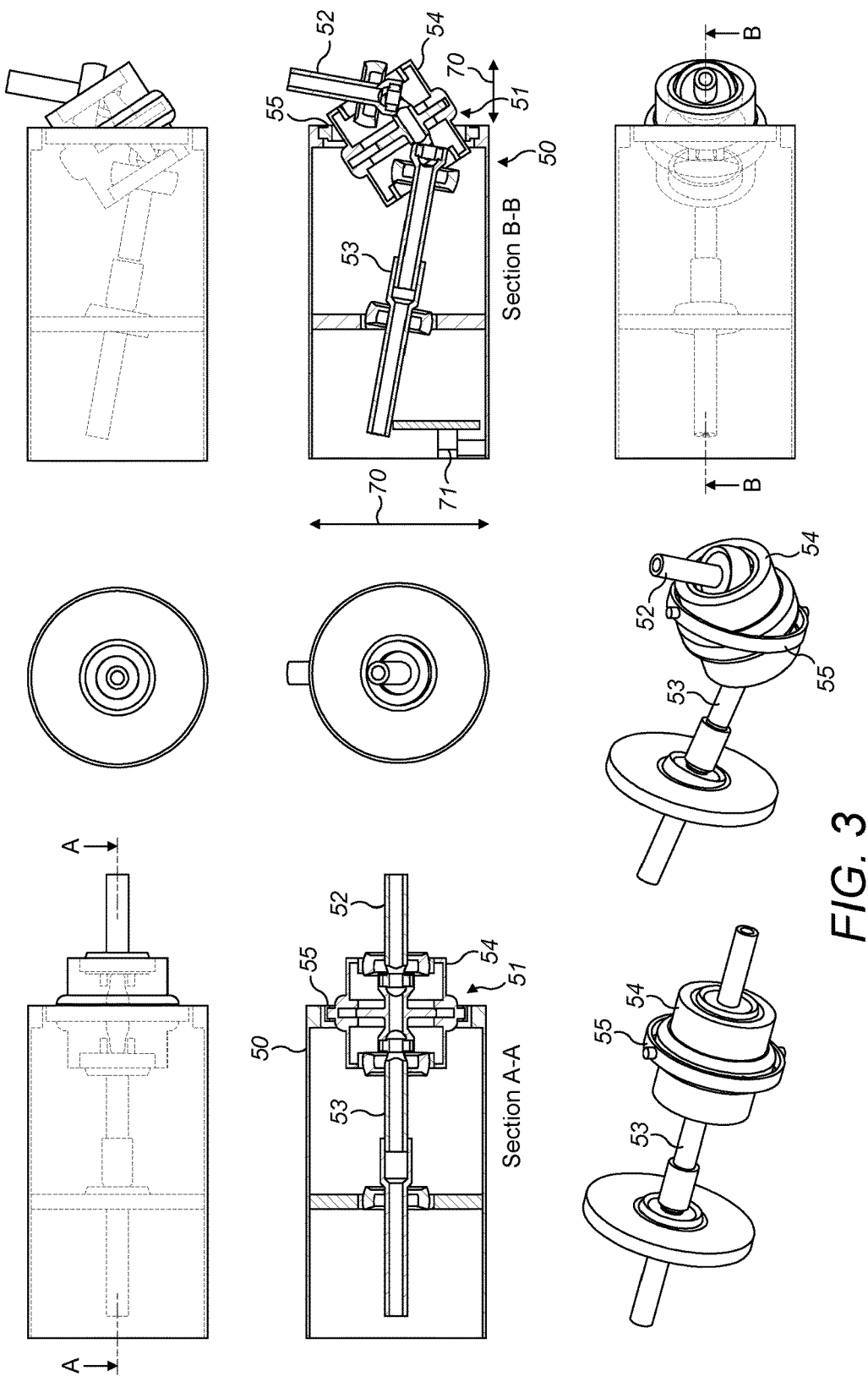
FIG. 3 shows various views of a second wrist joint for a surgical instrument.

FIG. 3 shows an alternative design of joint for a surgical instrument. In FIG. 3 the end-most part of the terminal link of the surgical instrument is shown at 50. The terminal link of the surgical instrument ends in a wrist joint 51 which carries an attachment 52 to which a surgical end effector can be attached. The joint 51 articulates the attachment 52 relative to the terminal link 50 of the surgical instrument. A control rod 53 runs inside the terminal link of the surgical instrument for controlling motion of the joint 51.

Figure 4:
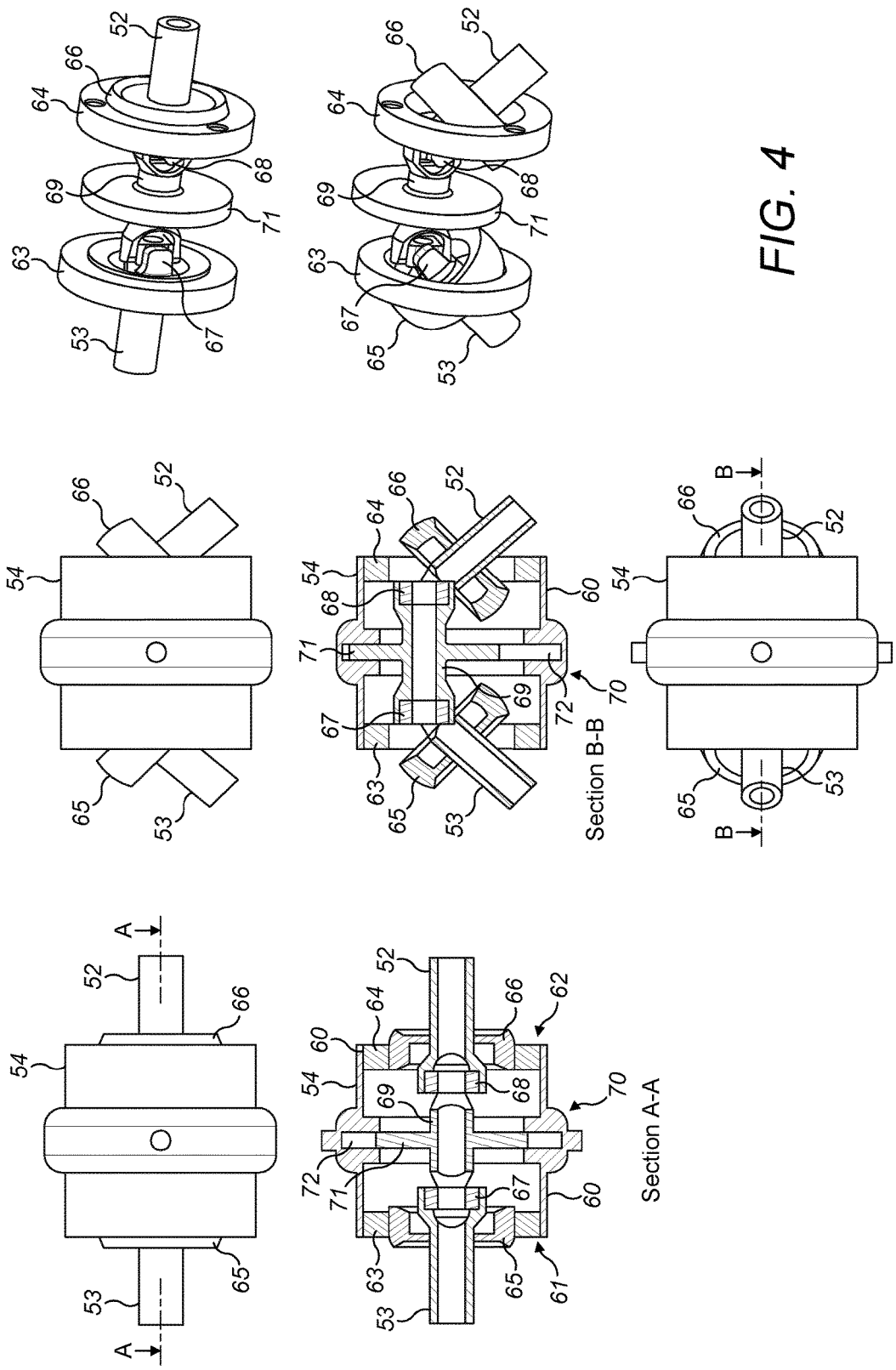
FIG. 4 shows various views of the second wrist joint for a surgical instrument.

The joint 51 comprises a can 54, which is shown in more detail in FIG. 4. An inner end of the can is attached to the distal end of the control rod 53. The attachment 52 is provided at the outer end of the can. The can is mounted relative to the terminal end of the surgical instrument in a joint 55. The joint 55 provides the can with freedom to rotate about axes orthogonal to the terminal link of the surgical instrument. In the example illustrated in the figures the spherical joint is provided by a gimbal ring, but it could be provided in other ways, for example it could be a spherical joint provided by a part-cup fast with the terminal end of the surgical instrument in which a part-ball formation of the can 54 is captive.

Referring to FIG. 4, the can comprises an outer shell 60. At each end of the shell is a spherical joint 61, 62 defined by a part-cup 63, 64 that is attached to the shell and a part-ball 65, 66 that is captive in the cup. The outer side of one part-ball 65 is coupled to the control rod 53. The outer side of the other part-ball 66 is coupled to the attachment 52. The inner side of each part-ball is provided with a universal joint 67, 68 whose centre is offset from the rotation centre of the respective part-ball. The universal joints 67, 68 are linked by a connecting rod 69. The connecting rod 69 is equipped with a mechanism 70 whose purpose is to prevent the connecting rod from rotating about axes transverse to its length. In the example of FIG. 4, that mechanism is provided by a flat slipper washer 71 which is attached to and extends transversely to the connecting rod 69. The slipper washer can slide snugly in an annular passageway 72 which also runs transversely to the connecting rod. The fact that the slipper washer is located in the annular passageway prevents the connecting rod from yawing.

Figure 5:
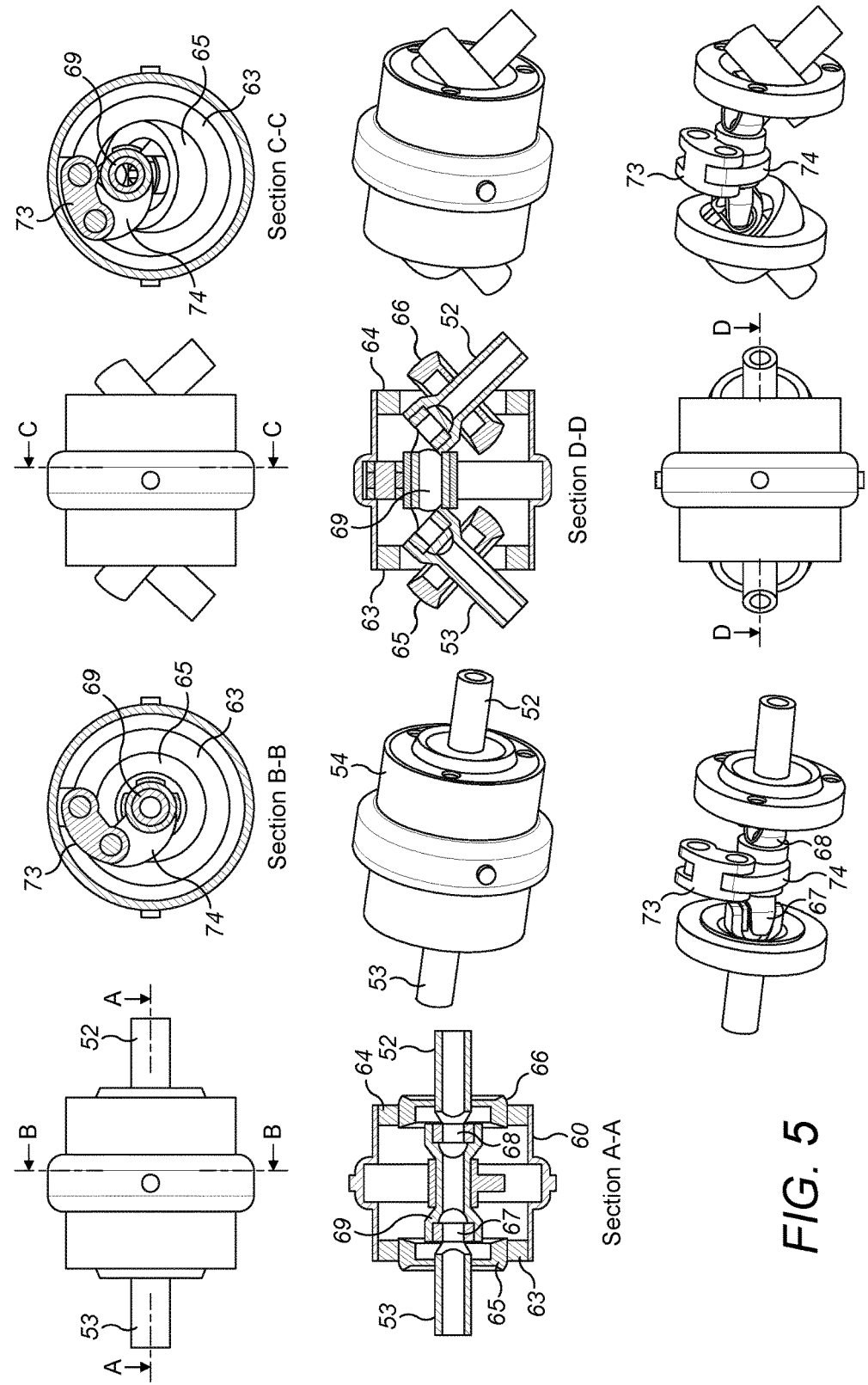
FIG. 5 shows various views of a third wrist joint for a surgical instrument.

FIG. 5 shows a similar can to that of FIG. 4. Like parts are designated the same in FIG. 5 as in FIG. 4. In FIG. 5 the mechanism for preventing the connecting rod from yawing is a pantograph having two links 73, 74 which are hinged relative to each other. One of the links, 73, is also hinged relative to the interior of the can. The other of the links, 74, carries a slip ring in which the connecting rod runs snugly.

As the part-balls 65, 66 rotate relative to the can the distance between the universal joints 67, 68 will change. To accommodate that the connecting rod could be made in two parts, one sliding snugly over the other. Alternatively, the attachment 52 and the control rod 53 could run slidably through the part-balls 65, 66 and terminate within the can in the universal joints. Then the connecting rod could be of fixed length.

When part-ball 65, which is connected to the control rod 53, is rotated relative to the can about an axis other than the can's longitudinal axis, that rotation causes the connecting rod 69 to translate laterally within the can. That in turn causes the part-ball 66 to rotate relative to the can in a way that mirrors the rotation of the part-ball 65.

Referring again to FIG. 3, the can is mounted in a spherical joint 55 relative to the terminal link of the surgical instrument. The control rod runs through a guide tube 75 that is mounted in a spherical joint 76 in the mid-part of the terminal link of the surgical instrument. That arrangement permits the control rod to rotate about that spherical joint and also to slide along its axis relative to that joint. When the control rod is moved so that its distal end moves transverse to the terminal link of the surgical instrument, that motion is transmitted to the inner part-ball 65 of the can. The can reacts against the spherical joint 55, resulting in rotation of the inner part-ball 65 relative to the can about an axis transverse to the terminal link of the instrument and also in rotation of the can relative to the instrument about an axis transverse to the terminal link of the instrument. The action of the connecting rod 69 means that the rotation of the inner part-ball is transmitted to the outer part-ball 66, causing it also to rotate relative to the can about an axis transverse to the terminal link of the instrument.

The terminal link of the surgical instrument of FIG. 3 is a rigid shaft, defined by a stiff outer tube 53. At the distal end of the tube is a spherical joint 21. Spherical joint 21 comprises a part-ball 24 which is captive in a part-cup 25. The part-cup is fast with the terminal link 20 of the surgical instrument. The part-ball is fast with the attachment 22. The spherical joint allows the attachment to move with three degrees of rotational freedom, but no translational freedom, relative to the terminal link of the surgical instrument.

As can be seen in FIG. 3, this arrangement allows the attachment 52 for the end effector to be deflected to relatively large angles relative to the terminal link of the surgical instrument. In a typical embodiment it may be expected that the attachment can be deflected through a cone approaching 180°.

It can also be seen from FIG. 3 that the joint 51 at the terminal end of the surgical instrument is relatively compact. This is illustrated at 70. The compactness of the joint also allows multiple similar surgical instruments to work in close proximity.

A further advantage of the joint of FIGS. 3 to 5 is that rotation of the control rod 53 about its longitudinal axis can be conveyed to the end effector with constant velocity. This may be useful if, for example, the end effector is a drill. It may also simplify the strategy needed to manage the motion of the control rod. To permit this behaviour it is preferable that the joint 55 in which the can 54 is mounted relative to the terminal link of the surgical instrument does not permit rotation of the can about the longitudinal axis of the terminal link of the surgical instrument. The joint 55 could be a gimbal joint.

The motion of the control rod 53 relative to the tube can be driven by any suitable means, for example electric motors 71 or hydraulic or pneumatic rams. The control rod can be elongated so that it runs from the distal end of the terminal link 50 to near the proximal end of the terminal link, with the result that those drive means can be located near the proximal end of the terminal link. That is convenient because it reduces the weight that is suspended near the distal end of the terminal link, making the terminal link easier to control.

The joints described above can be used in other applications. For example, the joints could be used for joints in robots other than surgical robots; and for joints other than wrist joints, whether in surgical robots or for other purposes. The joints could be used in non-robotic applications, for example in vehicles (e.g. in drive shafts or steering columns) or in other machinery.

The end effector could be engaged in the attachment 22, 52 by any suitable mechanism, for example by a screw, bayonet or snap fitting.

The can 54 need not enclose the connecting rod 69.

Figure 6:
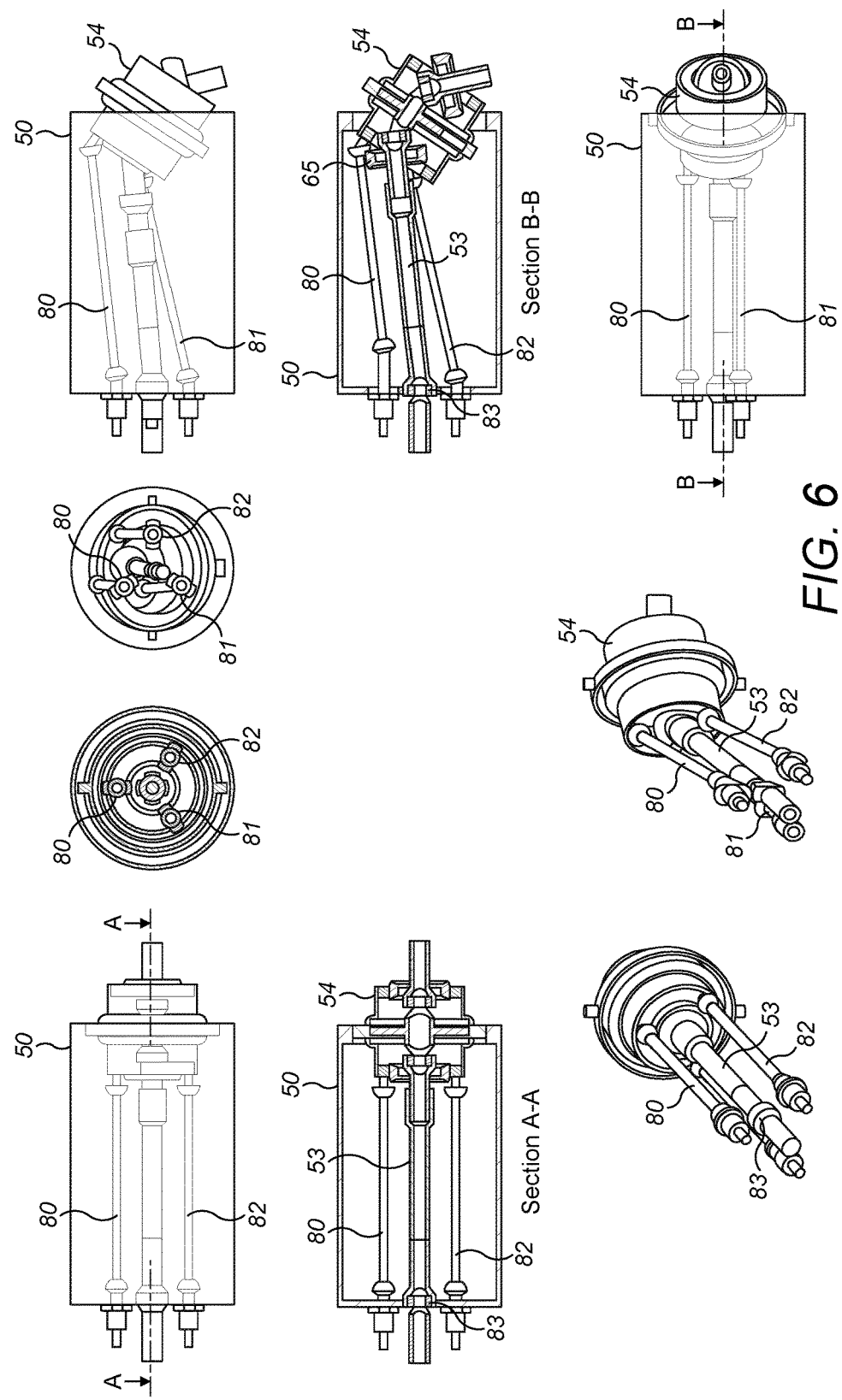
FIG. 6 shows a fourth wrist joint for a surgical instrument.

FIG. 6 shows a further way in which the can 54 could be controlled. In this mechanism three push rods 80, 81, 82 are attached to the inner end of the can, at locations spaced around the can. The push rods can be moved axially relative to the terminal link of the surgical instrument, e.g. by screw drives, to cause the can to adopt a desired location. The control rod 53 is mounted to a universal joint 83 within the terminal link of the surgical instrument, and is made in two parts, with one surrounding and being splined to the other in order to accommodate changes of distance between the universal joint 83 and its point of attachment to the inner part-ball 65. This arrangement is convenient in that the control rod 53 can readily be rotated by way of the universal joint 83 independently of the mechanism for setting the attitude of the end effector.

Figure 7:
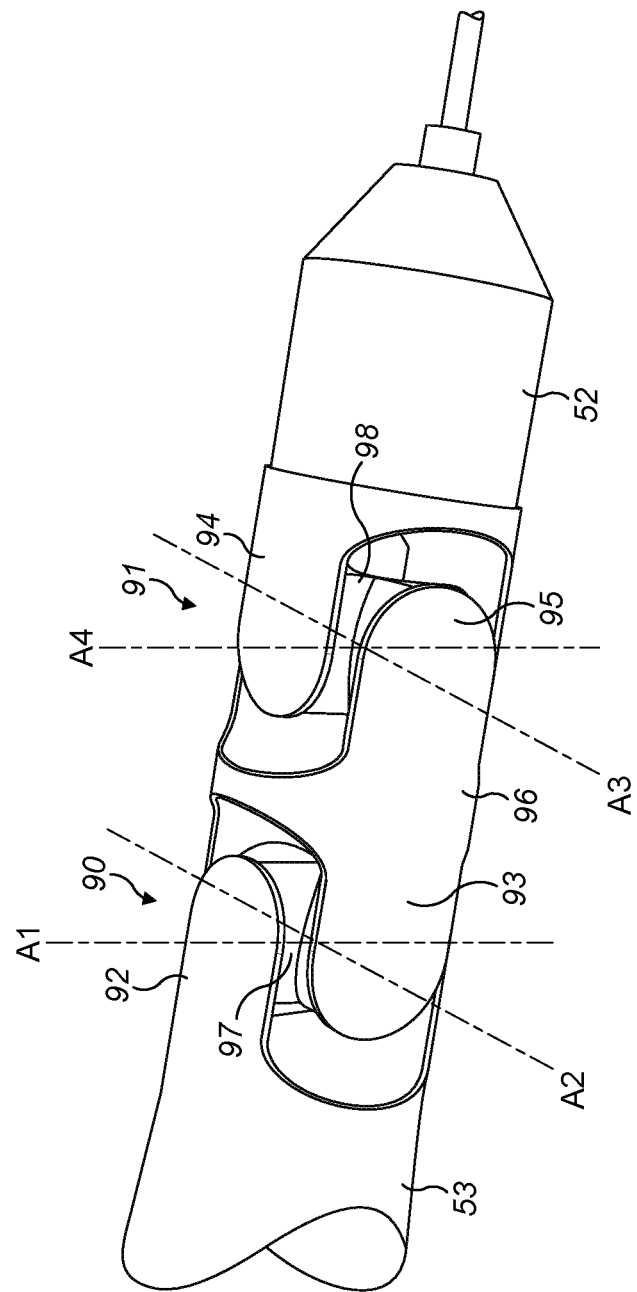
FIG. 7 shows a fifth wrist joint for a surgical instrument.

FIGS. 3 to 6 illustrate using a spherical joint to couple the control rod to the can and another spherical joint to couple the attachment to the can. Other joints may be used in these instances instead of a spherical joint. For example, a gimble joint may be used. As another example, a universal joint may be used. FIG. 7 illustrates an example in which two universal joints 90 and 91 are used to couple control rod 53 to attachment 52 via intermediate shaft 96. Control rod 53 terminates in U-joint 92 which rotates about axes A1 and A2. Intermediate shaft 96 comprises U-joint 93 which is arranged perpendicular to U-joint 92 and is coupled to U-joint 92 via cross-piece 97. U-joint 93 rotates about axes A1 and A2. Attachment 52 terminates in U-joint 94 which rotates about axes A3 and A4. Intermediate shaft 96 comprises U-joint 95 which is arranged perpendicular to U-joint 94 and perpendicular to U-joint 92 and is coupled to U-joint 94 via cross-piece 98. U-joint 95 rotates about axes A3 and A4.

Intermediate shaft 96 may house the components interior to the can shown in FIGS. 3 to 6. In this case the attachment 52 is mechanically slaved to the control rod 53 via the mechanisms described with respect to FIGS. 3 to 6 except that the universal joints 90 and 91 provide the articulation provided by the spherical joints in FIGS. 3 to 6. In other words, the rotation of universal joint 90 about axes A1 and A2 mirrors the rotation of universal joint 91 about axes A3 and A4. In an alternative implementation, the rotation of universal joint 90 about axes A1 and A2 is asymmetric to the rotation of universal joint 91 about axes A3 and A4. For example, the double universal joint may be constructed such that universal joint 90 has ~±90° of travel about axis A1 and ~±30° of travel about axis A2, and universal joint 91 has ~±30° of travel about axis A4 and ~±90° of travel about axis A3.

In this alternative implementation, the slaving may be accomplished mechanically by driving both joints from a common drive but with different gear ratios in the joint mechanisms. In the example given, a common drive input causes universal joint 90 to rotate around axis A1 and universal joint 91 to rotate around axis A4. However different gear ratios are used in the joint mechanisms, such that when driven, universal joint 90 rotates three times as far as universal joint 91. This would lead to both joints reaching the limit of their range at the same time. Another common drive input causes universal joint 90 to rotate about axis A2 and universal joint 91 to rotate about axis A3. Different gear ratios are used in the joint mechanisms, such that when driven, universal joint 91 rotates three times as far as universal joint 90. This would lead to both joints reaching the limit of their range at the same time. Alternatively the joints may be slaved electronically. In this case, each axis is independently controlled and software implemented to ensure the correct relationship between all the joint movements.

The attachment 52 and control rod 53 may be mechanically slaved together as illustrated in FIGS. 3 to 6. Alternatively, the attachment 52 and control rod 53 may be partially or fully electronically slaved to one another in order to provide the same range of motion described with respect to FIGS. 3 to 6.

Figure 8:
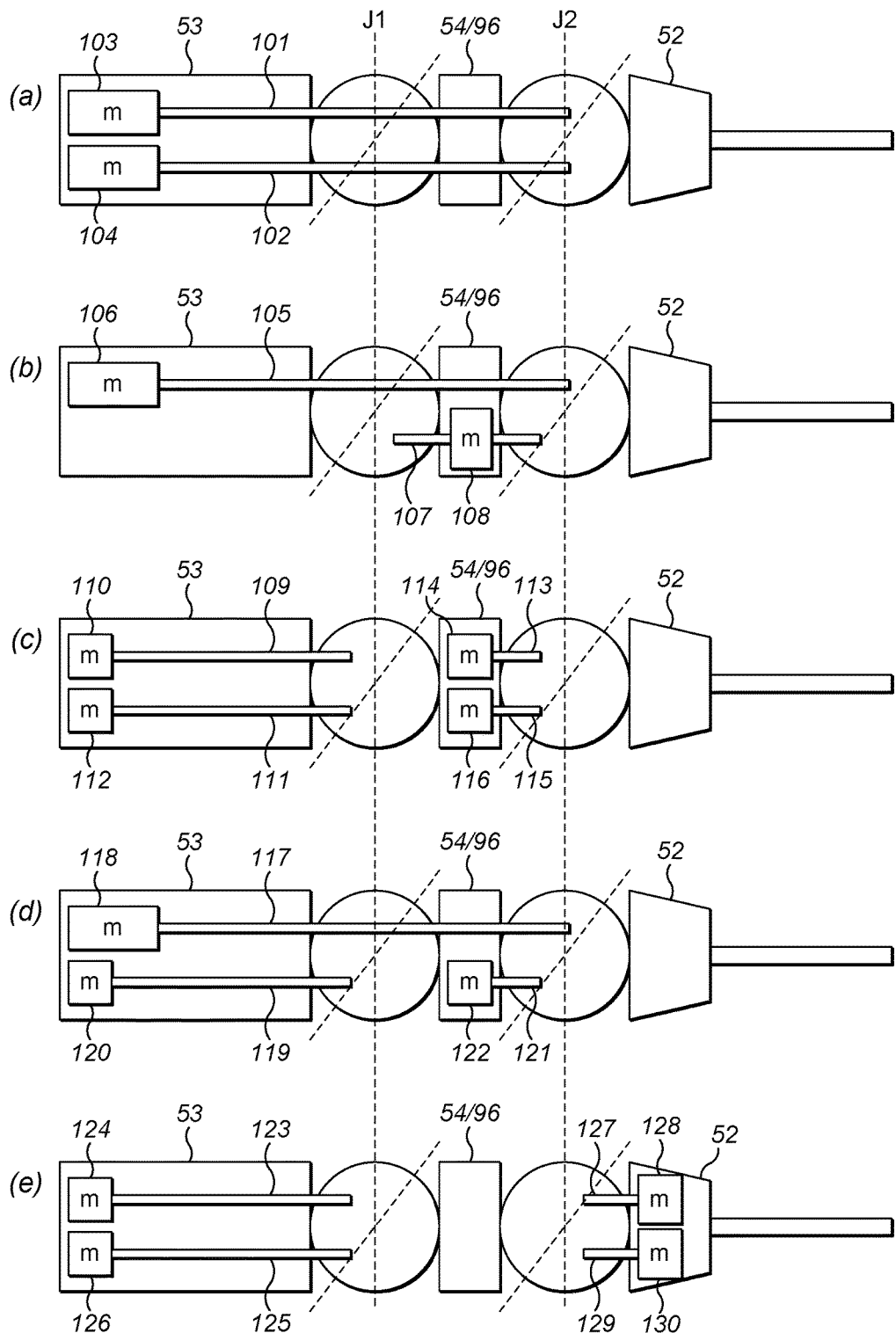
FIG. 8 shows example slaving arrangements for two links of a surgical instrument.

FIG. 8 illustrates some exemplary slaving arrangements for a first joint J1 which is the terminal joint of control rod 53 and a second joint J2 which is the terminal joint of attachment 52. Joints J1 and J2 may be spherical joints, universal joints, gimble joints or any other joints which enable the same articulation between the control rod 53 and the intermediate shaft 96/can 54 and the intermediate shaft 96/can 54 and the attachment 52 as described above.

In one implementation of FIG. 8(a), J1 and J2 are wholly electronically slaved together. In this case, control shaft 101 driven by motor 103 controls part of the motion of J1 and J2. The other part of the motion of J1 and J2 is controlled by control shaft 102 driven by motor 104. Control shaft 101 is coupled to J1 and terminates at J2. Control shaft 102 is coupled to J1 and terminates at J2. Motor 103 is located either in control rod 53 or further towards the base of the surgical instrument or robot arm. Motor 104 is located either in control rod 53 or further towards the base of the surgical instrument or robot arm. In the case of a double universal joint as shown in FIG. 7, rotation of the universal joint 90 about axis A1 is controlled by motor 103 via control shaft 101. Similarly, rotation of the universal joint 91 about axis A4 is controlled by motor 103 via control shaft 101. Rotation of the universal joint 90 about axis A2 is controlled by motor 104 via control shaft 102. Rotation of the universal joint 91 about axis A3 is controlled by motor 104 via control shaft 102. Motors 103 and 104 drive their respective control shafts to cause J1 and J2 to articulate in the same manner as if J1 and J2 were mechanically slaved together as described above.

In an alternative implementation of FIG. 8(a), J1 and J2 are mechanically slaved together by intermediate shaft 96/can 54, for example as discussed above with reference to FIGS. 3 to 7. Control shaft 101 driven by motor 103 terminates at J2. Motor 103 is located either in control rod 53 or further towards the base of the surgical instrument or robot arm. Control shaft 102 driven by motor 104 also terminates at J2. Motor 104 is located either in control rod 53 or further towards the base of the surgical instrument or robot arm. In the case of a double universal joint as shown in FIG. 7, rotation of the universal joint 91 about one axis A3 or A4 is controlled by motor 103 via control shaft 101. Similarly, rotation of the universal joint 91 about the other axis A3 or A4 is controlled by motor 104 via control shaft 102. J1 is mechanically slaved to J2, thus when J2 is driven by motors 103 and 104, J1 also moves in a manner determined by the manner in which J1 and J2 are mechanically slaved. In FIG. 8(a) the joint J2 which is the most distal of joints J1 and J2 from the control rod 53 is driven by motors 103 and 104. Alternatively, the control shafts 101 and 102 may be attached to and drive joint J1, and joint J2 moves in a manner determined by the mechanical slaving between J1 and J2.

In one implementation of FIG. 8(b), J1 and J2 are wholly electronically slaved together. In this case, control shaft 105 driven by motor 106 controls part of the motion of J1 and J2. The other part of the motion of J1 and J2 is controlled by control shaft 107 driven by motor 108. Control shaft 105 is coupled to J1 and terminates at J2. Control shaft 107 driven by motor 108 terminates at one end at J1 and at the other end at J2. Motor 108 is located in intermediate shaft 96 between J1 and J2. Motor 106 is located either in control rod 53 or further towards the base of the surgical instrument or robot arm. In the case of a double universal joint as shown in FIG. 7, rotation of the universal joint 90 about axis A1 is controlled by motor 106 via control shaft 105. Similarly, rotation of the universal joint 91 about axis A4 is controlled by motor 106 via control shaft 105. Rotation of the universal joint 90 about axis A2 is controlled by motor 108 via control shaft 107. Rotation of the universal joint 91 about axis A3 is controlled by motor 108 via control shaft 107. Motors 103 and 104 drive their respective control shafts to cause J1 and J2 to articulate in the same manner as if J1 and J2 were mechanically slaved together as described above.

In one implementation of FIG. 8(d), J1 and J2 are wholly electronically slaved together. In this case, control shaft 117 driven by motor 118 controls part of the motion of J1 and J2. Control shaft 117 is coupled to J1 and terminates at J2. The other part of the motion of J1 is controlled by control shaft 119 driven by motor 120. The other part of the motion of J2 is controlled by control shaft 121 driven by motor 122. Motor 122 is located in intermediate shaft 96 between J1 and J2. Motor 118 is located either in control rod 53 or further towards the base of the surgical instrument or robot arm. Motor 120 is located either in control rod 53 or further towards the base of the surgical instrument or robot arm. In the case of a double universal joint as shown in FIG. 7, rotation of the universal joint 90 about axis A1 is controlled by motor 118 via control shaft 117. Similarly, rotation of the universal joint 91 about axis A4 is controlled by motor 118 via control shaft 117. Rotation of the universal joint 90 about axis A2 is controlled by motor 120 via control shaft 119. Rotation of the universal joint 91 about axis A3 is controlled by motor 122 via control shaft 121. Motors 118, 120 and 122 drive their respective control shafts to cause J1 and J2 to articulate in the same manner as if J1 and J2 were mechanically slaved together as described above.

FIG. 8(c) illustrates an arrangement in which J1 and J2 are wholly electronically slaved together. Control shaft 109 driven by motor 110 terminates at J1. Motor 110 is located either in control rod 53 or further towards the base of the surgical instrument or robot arm. Control shaft 111 driven by motor 112 terminates at J1. Motor 112 is located either in control rod 53 or further towards the base of the surgical instrument or robot arm. Control shaft 113 driven by motor 114 terminates at one end in intermediate shaft 96 between J1 and J2 and at the other end at J2. Motor 114 is located in intermediate shaft 96 between J1 and J2. Control shaft 115 driven by motor 116 terminates at one end in intermediate shaft 96 between J1 and J2 and at the other end at J2. Motor 116 is located in intermediate shaft 96. Motor 110 drives J1 to articulate about one of its axes. Motor 112 drives J1 to articulate about the other of its axes. Motor 114 drives J2 to articulate about one of its axes. Motor 116 drives J2 to articulate about the other of its axes. Motors 110, 112, 114 and 116 drive their respective control shafts to cause J1 and J2 to articulate in the same manner as if J1 and J2 were mechanically slaved together as described above.

FIG. 8(e) illustrates an arrangement in which J1 and J2 are wholly electronically slaved together. Control shaft 123 driven by motor 124 terminates at J1. Motor 124 is located either in control rod 53 or further towards the base of the surgical instrument or robot arm. Control shaft 125 driven by motor 126 terminates at J1. Motor 126 is located either in control rod 53 or further towards the base of the surgical instrument or robot arm. Control shaft 127 driven by motor 128 terminates at one end in attachment 52 and at the other end at J2. Motor 128 is located in attachment 52. Control shaft 129 driven by motor 130 terminates at one end in attachment 52 at the other end at J2. Motor 130 is located in attachment 52. Motor 124 drives J1 to articulate about one of its axes. Motor 126 drives J1 to articulate about the other of its axes. Motor 128 drives J2 to articulate about one of its axes. Motor 130 drives J2 to articulate about the other of its axes. Motors 128, 130, 124 and 126 drive their respective control shafts to cause J1 and J2 to articulate in the same manner as if J1 and J2 were mechanically slaved together as described above.

The control shafts of FIG. 8 may drive the respective joints about their axes using, for example, a worm and spur gear or a worm and face gear. The control shafts may be coaxial. For example, control shafts 117 and 119 in FIG. 8(d) may be coaxial shafts where the inner shaft 117 drives J2 and the outer shaft 119 drives J1. Alternatively, the joints may be driven from an off-axis control shaft which drives the joints via a bevel gear, worm gear or offset hypoid gear. Suitably, the control shafts are hollow in order to allow for control cables to pass through them.

Suitably, the motors and drive elements are located towards the base of the robot arm. This reduces the weight suspended near the distal end of the attachment, making the attachment easier to control. It also reduces the required strength of the other arm joints and surgical instrument joints, enabling the arm and surgical instrument to be lighter and hence easier to control.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic instrument comprising an arm extending between a robot arm connection and an attachment for an end effector, the arm comprising:
   a first arm part;
   a second arm part distal of the first arm part; and an articulation whereby the first and second arm parts are coupled together, the articulation comprising:

an intermediate coupling having a housing and an articulation mechanism borne by the housing, the housing being attached to the first arm part by a joint permitting the housing and the first arm part to rotate relative to each other about at least two mutually offset axes, and the articulation mechanism comprising:

a first coupler having rotational freedom relative to the housing, a second coupler having rotational freedom relative to the housing and a connector extending between the first and second couplers so that rotation of the first coupler relative to the housing can cause rotation of the second coupler relative to the housing; and a control rod connected to the first coupler and extending proximally of the first coupler along the first arm part;

the second arm part being connected to the second coupler.

2. The robotic instrument as claimed in claim 1, wherein the intermediate coupling comprises an arrangement configured to resist rotation of the connector about axes transverse an axis between a first location where the connector is connected to the first coupler and a second location where the connector is connected to the second coupler.

3. The robotic instrument as claimed in claim 2, wherein the said arrangement comprises a guide piece extending transverse to the connector and a guideway fast with the housing in which the guidepiece can run.

4. The robotic instrument as claimed in claim 2, wherein the said means comprises a pair of arms that are hinged relative to each other, one of the arms further being hinged relative to the housing and the other of the arms being coupled to the connector.

5. The robotic instrument as claimed in claim 4, wherein the said other of the arms has a cylindrical opening through which the connector can slide.

6. The robotic instrument as claimed in claim 1, wherein the articulation is a wrist joint of the robotic instrument.

7. The robotic instrument as claimed in claim 1, wherein the second arm part is an attachment for an end effector.

8. The robotic instrument as claimed in claim 1, wherein the control rod is coupled to the first arm part via a spherical joint.

9. The robotic instrument as claimed in claim 1, wherein the control rod is coupled to the first arm part via a universal joint.

10. The robotic instrument as claimed in claim 1, wherein the first arm part is defined by a structural tube and the control rod runs inside that tube.

* * * * *